US009464009B2

(12) United States Patent
Meessen et al.

(10) Patent No.: US 9,464,009 B2
(45) Date of Patent: Oct. 11, 2016

(54) REMOVAL OF UREA AND AMMONIA FROM EXHAUST GASES

(75) Inventors: Jozef Hubert Meessen, Wijlre (NL); Pantelis Orfanidis, Vouliagmeni (GR)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 13/496,192

(22) PCT Filed: Aug. 10, 2010

(86) PCT No.: PCT/EP2010/061588
§ 371 (c)(1), (2), (4) Date: May 29, 2012

(87) PCT Pub. No.: WO2011/032786
PCT Pub. Date: Mar. 24, 2011

(65) Prior Publication Data

US 2012/0240649 A1 Sep. 27, 2012

(30) Foreign Application Priority Data

Sep. 16, 2009 (EP) .................................... 09170447

(51) Int. Cl.
*B01D 47/00* (2006.01)
*C05C 9/00* (2006.01)
*C01C 1/12* (2006.01)
*C05C 3/00* (2006.01)
*C07C 273/16* (2006.01)

(52) U.S. Cl.
CPC . *C05C 9/00* (2013.01); *C01C 1/12* (2013.01); *C05C 3/00* (2013.01); *C07C 273/16* (2013.01)

(58) Field of Classification Search
None
See application file for complete search history.

(56) References Cited

U.S. PATENT DOCUMENTS 2,902,342 A * 9/1959 Kerley, Jr. ................ C05B 7/00 422/618
3,928,015 A 12/1975 Siegel et al.
2008/0092614 A1* 4/2008 Ingels et al. ...................... 71/30
2009/0084149 A1* 4/2009 Van Der Werf et al. ......... 71/28

FOREIGN PATENT DOCUMENTS

DE 101 33 935 1/2003
JP 9227493 A * 2/1997
WO WO-01/51429 7/2001
WO WO-2006/111331 10/2006

OTHER PUBLICATIONS

Translation of patent JP9227493A (Feb. 9, 1997), Hidetsugu et al.*
Translation of patent DE10133935A1 (Jan. 30, 2003), Horst et al.*
Matthias Potthoff, "Innovative ammonia emission reductions", Nitrogen+Syngas, Jul.-Aug. 2008, pp. 39-41.*
IFC, "Environmental, Health, and Safety Guidelines for Nitrogenous Fertilizer Production", Apr. 30, 2007.*
Database WPI, accession No. 1997-486394 (1997).
International Search Report for PCT/EP2010/061588, mailed Sep. 6, 2010, 3 pages.

* cited by examiner

*Primary Examiner* — Jonathan Johnson
*Assistant Examiner* — Anita Nassiri Motlagh
(74) *Attorney, Agent, or Firm* — Morrison & Foerster LLP

(57) ABSTRACT

The invention relates to a method for recovery of urea dust and ammonia from a gas stream by contacting said gas stream with an aqueous sulphuric acid solution, thus forming an acid solution of ammonium sulphate and urea, characterized in that the acid solution is concentrated to a melt comprising less than 5 wt % of water, which melt is subsequently transferred into solid particles comprising urea and ammonium sulphate.

15 Claims, 3 Drawing Sheets

18
16
11
1
21
2
12
15
22
13
3
23
4
17

REMOVAL OF UREA AND AMMONIA FROM EXHAUST GASES

CROSS-REFERENCE TO RELATED APPLICATIONS

This application is the national phase of PCT application PCT/EP2010/061588 having an international filing date of 10 Aug. 2010, which claims benefit of European patent application No. 09170447.8 filed 16 Sep. 2009. The contents of the above patent applications are incorporated by reference herein in their entirety.

Urea dust and ammonia are known to be present in exhaust gases from urea plants, urea granulation towers, urea prilling towers and chemical fertilizer plants. Such plants in particular release waste air streams that contain dust and ammonia resulting from various process steps. This air stream must be purified before being passed into the environment or recycled back into the process. Such waste air stream result in particular from granulation, prilling and product cooling process steps.

JP9227493 describes a method for recovery of urea dust and ammonia from such a gas stream by contacting said gas stream with an aqueous sulphuric acid solution, thus forming an acid solution of ammonium sulphate and urea.

A disadvantage of the known process is, that the resulting product is a solution, which can hardly be used as a fertilizer due to its high transport costs.

As described in DE10133935 it is a desire to add sulphur to nitrogen containing fertilizers. It is a further desire to reduce pollution from industrial activities and in particular from fertilizer production plants.

Surprisingly it has been found that these two desire could be combined at an economically attractive scale by concentrating the acid solution to a melt, comprising less than 5 wt % of water, which melt is subsequently transferred into solid particles comprising urea and ammonium sulphate.

Another problem of the method described in JP9227493 is that the resulting solution is an acidic solution, which is not only a disadvantage for the soil wherein it is used as a fertilizer, but it results in corrosion in metal equipment used to concentrate, handle and transport the acidic solution, unless special, high cost, materials of construction are used for such metal equipment.

This problem can be solved, by adding ammonia to the acidic solution before the acidic solution is concentrated, thus forming a neutralized solution of ammonium sulphate and urea in water.

A further problem of the method described in JP9227493 is that the sulphur (S) to nitrogen (N) ratio in the produced liquid fertilizer is depending on the ammonia to urea ratio in the gas stream from which the urea and ammonia are recovered. This poses a problem since:

Depending on the source of this gas stream, this ratio of ammonia to urea in this gas stream, and the resulting S/N ratio in the produced fertilizer may not be stable over time. This therefore results in a non-stable quality of the produced fertilizer.

Depending on the soil conditions where the fertilizer is applied, an optimal S/N ratio can be defined from an agronomic point of view. The coincidental ammonia to urea ratio in said gas stream in general will not result in the same optimal S/N ratio in the fertilizer produced.

These two disadvantages can be overcome by adding an additional amount of ammonium sulphate to the concentrated melt, or to the solution to be concentrated, such that the S/N ratio in the produced fertilizer can be controlled to any desired value. By changing the amount of additional ammonium sulphate that is added as a function of the ammonia to urea ratio in the gas stream, this S/N ratio also can be controlled in a stable way over time and to the optimal S/N ratio from an agronomic point of view.

Preferably the neutralized solution is concentrated by vaporization of at least part of the water phase, thus forming water vapor and a melt comprising less than 5 wt % of water.

More preferably the vaporization is carried out in more than one step until the amount of water is less than 5 wt %. This allows reducing the amount of water in the melt to less than 1 wt %, and even to less than 0.3 wt %.

Subsequently, the melt is transferred into urea and ammonium sulphate comprising solid particles. This process can be carried out in a granulator, or prilling tower. However this would reintroduce (on a smaller scale) the problem of ammonia and dust loaded air. Therefore this process is preferably carried out in a pelletizer, comprising a feeding device, a solidification/cooling belt and a device to remove the formed pellets from the belt, by feeding a urea-comprising liquid to the feeding device from which droplets of the urea-comprising liquid are dosed to the belt, whereon the urea-comprising droplets solidify, where after the formed urea-comprising particles are removed from the belt. The belt is cooled from the other side, preferably by means of cooling water. The advantage of using said pelletizer instead of a granulator is twofold:

1. The scale wherein the method of the invention is generally performed generally allows for pelletizing to be more economical as compared to granulation or prilling.
2. Pelletizing using the above mentioned process does not produce a large dust/ammonia loaded air flow, which would reintroduce the original problem albeit on a smaller scale.

The invention will be explained in greater detail below, using the drawings.

Figure 1:
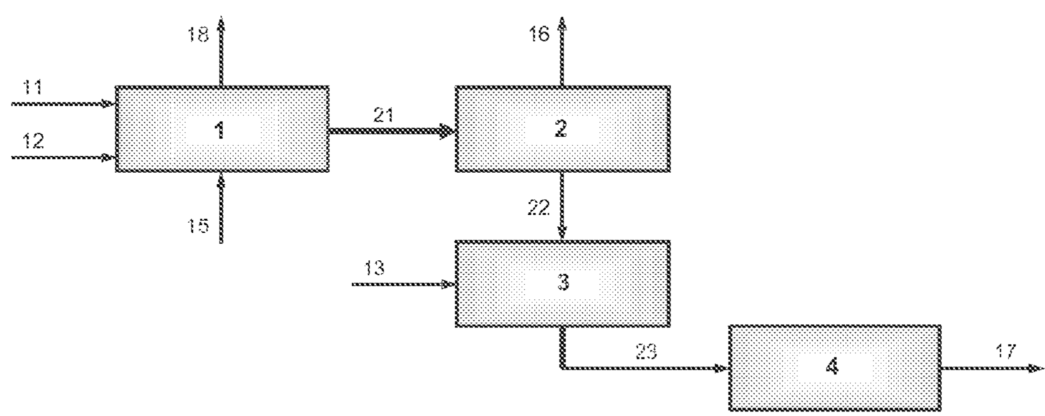
FIG. 1 is a schematic system for implementing an embodiment of the present invention.

A system for implementing the method of the invention is shown in FIG. 1. A gas stream comprising air, urea and ammonia (11) is contacted in a scrubber (1) with an aqueous sulphuric acid solution (12), thus forming an acidic solution of urea and ammonium sulphate.

Scrubber (1) can be selected from any of the wet-type scrubbers well known in the industry. It may, for instance, be selected from the type of scrubbers as summarized in Chemical Engineers Handbook (Perry and Chilton), fifth edition, page 20-94 to 20-103. Stream 11 usually has a relative high temperature (70-110° C.), and may be rather dry. As a result of this, quite some water may evaporate in the scrubber. In many cases it therefore will be required to add make-up water (15) to the scrubber in order to assure that the concentration of urea and ammonium sulphate in the liquid phase in the scrubber remains below the solubility limits. Depending on the type of scrubber selected, circulation of acidic urea/ammonium sulphate (UAS) solution over the scrubber (not shown in the figure) may be required for proper removal of ammonia and dust from the air stream.

The cleaned air leaves the scrubber via line 18.

The acidic solution of urea and ammonium sulphate is passed through line (21) to concentration unit (2), which may comprise at least one concentrator Water vapor leaves the concentration unit (2) via line (16). In the concentration unit (2), the acidic solution of urea and ammonia is concentrated to a melt, comprising less than 5 wt % of water. The concentration unit (2) may consist of one or more evaporators in parallel or in series. These evaporators may be selected from evaporators, as they are well known in the process industry. They may, for instance, be selected from the evaporators as summarized in Chemical Engineers Handbook (Perry and Chilton), fifth edition, pages 11-27 to 11-38. Urea is vulnerable for decomposition (e.g. hydrolyses and biuret formation) at high temperatures and at long residence time. For this reason the evaporators are usually selected from the types 'falling film' or 'Long tube vertical' (refer to FIG. 11-16 in Chemical Engineers Handbook (Perry and Chilton), fifth edition) since they offer low residence time. Also, in order to minimize urea decomposition, the evaporators preferably are operated under vacuum, in order to minimize the required temperature. The vacuum in the evaporators can be maintained using a system of vacuum condensers and steam-jet ejectors (not shown in the figure), or other systems, that are well known in the industry.

The concentrated UAS melt leaves the concentration unit via line (22) to mixer (3). Solid ammonium sulphate is also introduced into the mixer (3), in order to increase the ammonium sulphate to urea ratio to the desired value. The dosing of ammonium sulphate to mixer (3) is controlled in such a way that a stable ammonium sulphate to urea ratio is obtained in the final product (17). Mixer (3) may be selected from any of the solid/liquid mixers well known in the industry. It may e.g. be selected from the mixers as summarized in Chemical Engineers Handbook (Perry and Chilton), fifth edition, pages 19-3 to 19-25. Selection of the mixer mainly is depending on the required ammonium sulphate to urea ratio. In case low concentrations of ammonium sulphate are required, then the solid concentration in slurry (23) will be low. In that case it will be sufficient to select the mixer from the class of 'agitating mixers'. In case higher concentrations of ammonium sulphate are required, then the mixer more effectively can be selected of the class of 'paste and viscous material mixing' equipment. From the mixer slurry of solid ammonium sulphate in a urea/ammonium sulphate $(UAS)^+$ melt is transported via line (23) to the solid shaping step (4).

The solid shaping step (4) may consist of granulation, prilling or pelletizing. It is of special advantage to select pelletizing as solid shaping process, since such a pelletizing process does not result in dust and ammonia loaden off-gas as is the case with prilling and granulation processes. An example of such a pelletizing process is described in WO 2006/111331 A1. The final product, a solid mixture of urea and ammonium sulphate, leaves the process via line (17).

Figure 2:
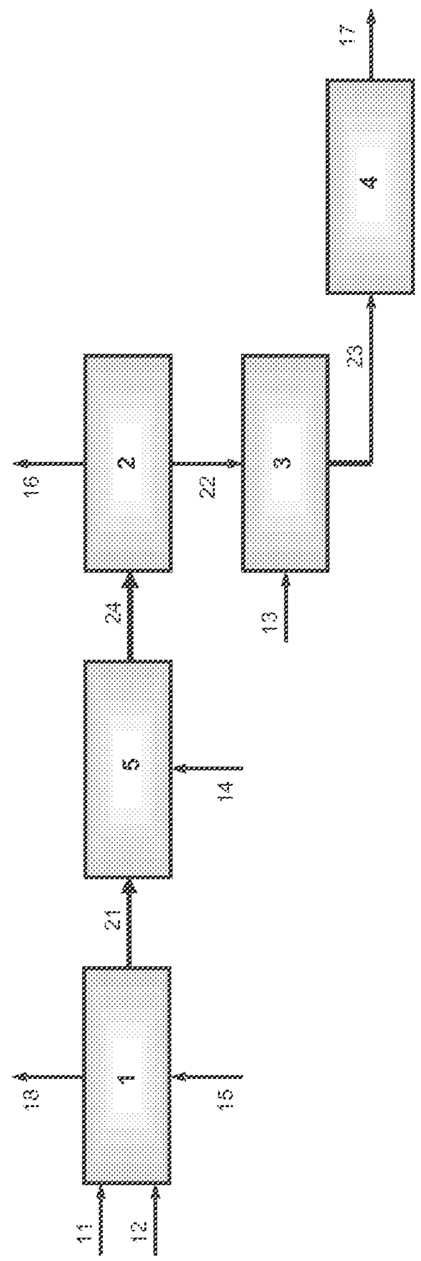
FIG. 2 is schematic system for implementing of another embodiment of the present invention.

FIG. 2 shows a system for implementing the method of the invention, wherein ammonia or ammonia water (14) is added to the acid solution in a neutralizer (5) before the acidic solution (21) is concentrated, thus forming a neutralized solution of urea and ammonium sulphate in water that is passed through line (24) to the concentration unit (2). The neutralizing process (5), may be accommodated in a mixing vessel with agitator, as well known in the industry. Taking into account the strong chemical affinity between sulphuric acid and ammonia, the neutralizing process may even be accommodated in a much simpler way, e.g. by supplying turbulent flow and sufficient residence time in the process line that transports UAS solution 24 to the concentration unit (2).

All other elements shown in FIG. 2 are similar to the elements in FIG. 1 and therefore are not further described here.

Figure 3:
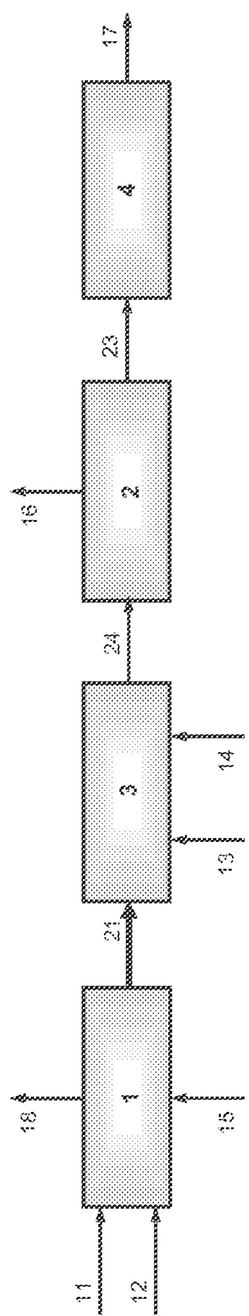
FIG. 3 is a schematic system for implementing of a further embodiment of the present invention.

FIG. 3 shows a further embodiment of the invention. The embodiment as shown in FIG. 3 offers special advantages over those as shown in FIGS. 1 and 2, in case the required ammonium sulphate to urea ratio in the final UAS product is limited. A gas stream comprising air, urea and ammonia (11) is contacted in a scrubber (1) with an aqueous sulphuric acid solution (12), thus forming an acidic solution of urea and ammonium sulphate. The cleaned air leaves the scrubber via (18). Make-up water is introduced into the scrubber via (15), in such an amount that no solids are formed in the streams (21) and (24) The formed acidic solution of urea and ammonium sulphate leaves the scrubber via (21), to be introduced in mixer (3). $NH_3$ (or ammonia water) is introduced into mixer (3) via line (14) in such an amount that the excess sulphuric acid present in (21) is neutralized. Additional solid ammonium sulphate is added to mixer (3) via line (13). Mixer (3) is an agitated vessel, where proper agitation ensures that all of the solid ammonium sulphate that is added to the mixer is dissolved before the enriched UAS solution leaves the mixer via (24) to concentration unit (2).

In the same way as described for FIG. 1, in concentration unit (2), the UAS solution is concentrated to such an extend that the UAS melt leaving the concentration unit via (23) has a water content of less the 5% by weight. This concentrated melt is transformed into a solid UAS product in solid shaping unit (4) in the same way as described for FIG. 1.

As compared to the process as described under FIG. 2, FIG. 3 offers the advantage that the process steps (5, neutralizer) and (3, mixer) now are combined in one step (3, mixer). This offers the advantage of lower capital investment for the process as described under FIG. 3. An advantage of the process as described under FIG. 2 as compared to the process as described under FIG. 3 is that the ammonium sulphate concentration in concentration step (2) can be higher without risking line blockage. Therefore the application of the process as described under FIG. 3 is limited to such cases, where the desired S/N ratio in product (17) is limited to such a value that the $UAS^+$ melt (23) contains no solid ammonium sulphate, or only such a limited quantity of solid ammonium sulphate that stream (23) remains a transportable slurry.

The invention claimed is:

1. A method for preparing a urea/ammonium sulfate (UAS) fertilizer from urea dust and ammonia in a gas stream which comprises contacting said gas stream with an aqueous sulphuric acid solution, thus forming an acid solution of ammonium sulphate and urea; followed by adding ammonia to the acid solution, thus forming a neutralized solution of urea and ammonium sulphate (AS) in water, followed by concentrating said neutralized solution to a melt comprising less than 5 wt % of water, and mixing the melt with an additional amount of ammonium sulphate, followed by transforming said melt into solid particles comprising urea and ammonium sulphate as a UAS fertilizer, wherein said gas stream is an exhaust waste gas from a urea plant, a urea-granulation tower, a urea-prilling tower or chemical fertilizer plant, and which exhaust waste gas stream is the sole source of the urea in the UAS fertilizer.

2. The method of claim 1, which further comprises vaporizing at least part of the water phase of the neutralized solution, thus forming water vapor and a melt comprising less than 5 wt % of water.

3. The method of claim 2, wherein said vaporizing is carried out in more than one step until the amount of water in the melt is less than 5 wt %.

4. The method of claim 1, which further comprises mixing the solution with an additional amount of ammonium sulphate before concentrating.

5. The method of claim 1, wherein said transforming is conducted in a pelletizer, said pelletizer comprising a feeding device, a belt and a device to remove the formed pellets from the belt, wherein said melt is transferred to said pelletizer by feeding the UAS-comprising liquid to the feeding device from which droplets of the UAS-comprising liquid are dosed to the belt, whereon the UAS-comprising droplets solidify followed by removing the formed UAS-comprising particles from the belt.

6. A method for preparing a UAS fertilizer from urea dust and ammonia in a gas stream which comprises contacting said gas stream with an aqueous sulphuric acid solution, thus forming an acid solution of ammonium sulphate and urea; followed by adding ammonia to the acid solution, thus forming a neutralized solution of urea and ammonium sulphate in water, followed by concentrating said neutralized solution to a melt comprising less than 5 wt % of water, followed by transforming said melt into solid particles comprising urea and ammonium sulphate in a pelletizer, said pelletizer comprising a feeding device, a belt and a device to remove the formed pellets from the belt, wherein said melt is transferred to said pelletizer by feeding the UAS-comprising liquid to the feeding device from which droplets of the UAS-comprising liquid are dosed to the belt, whereon the UAS-comprising droplets solidify to obtain a UAS fertilizer followed by removing the formed UAS-comprising particles from the belt to recover said UAS fertilizer, wherein said gas stream is an exhaust waste gas from a urea plant, a urea-granulation tower, a urea-prilling tower or chemical fertilizer plant, and which exhaust waste gas stream is the sole source of the urea in the UAS fertilizer.

7. The method of claim 6, which further comprises vaporizing at least part of the water phase of the neutralized solution, thus forming water vapor and a melt comprising less than 5 wt % of water.

8. The method of claim 7, wherein said vaporizing is carried out in more than one step until the amount of water in the melt is less than 5 wt %.

9. The method of claim 6, which further comprises mixing the melt with an additional amount of ammonium sulphate.

10. The method of claim 6, which further comprises mixing the solution with an additional amount of ammonium sulphate before concentrating.

11. A method for preparing a UAS fertilizer from urea dust and ammonia of a gas stream which comprises contacting said gas stream with an aqueous sulphuric acid solution, thus forming an acid solution of ammonium sulphate and urea; followed by adding ammonia to the acid solution, thus forming a neutralized solution of urea and ammonium sulphate in water and mixing the solution with an additional amount of solid ammonium sulphate, followed by concentrating said neutralized solution to a melt comprising less than 5 wt % of water, followed by transforming said melt into solid particles comprising urea and ammonium sulphate, thus obtaining UAS fertilizer wherein said gas stream is an exhaust waste gas from a urea plant, a urea-granulation tower, a urea-prilling tower or chemical fertilizer plant, and which exhaust waste gas stream is the sole source of the urea in the UAS fertilizer.

12. The method of claim 11, which further comprises vaporizing at least part of the water phase of the neutralized solution, thus forming water vapor and a melt comprising less than 5 wt % of water.

13. The method of claim 12, wherein said vaporizing is carried out in more than one step until the amount of water in the melt is less than 5 wt %.

14. The method of claim 11, which further comprises mixing the melt with an additional amount of ammonium sulphate.

15. The method of claim 11, wherein said transforming is conducted in a pelletizer, said pelletizer comprising a feeding device, a belt and a device to remove the formed pellets from the belt, wherein said melt is transferred to said pelletizer by feeding the UAS-comprising liquid to the feeding device from which droplets of the UAS-comprising liquid are dosed to the belt, whereon the UAS-comprising droplets solidify followed by removing the formed UAS-comprising particles from the belt.

* * * * *